United States Patent
Thielert et al.

(10) Patent No.: US 9,045,708 B2
(45) Date of Patent: Jun. 2, 2015

(54) METHOD AND APPARATUS FOR MAKING A METHANE-RICH GAS FROM SYNGAS

(75) Inventors: Holger Thielert, Dortmund (DE); Johannes Menzel, Waltrop (DE)

(73) Assignee: TYSSENKRUPP UHDE GMBH, Dortmund (DE)

( * ) Notice: Subject to any disclaimer, the term of this patent is extended or adjusted under 35 U.S.C. 154(b) by 0 days.

(21) Appl. No.: 13/876,002

(22) PCT Filed: Oct. 5, 2011

(86) PCT No.: PCT/EP2011/067369
§ 371 (c)(1),
(2), (4) Date: Apr. 25, 2013

(87) PCT Pub. No.: WO2012/045766
PCT Pub. Date: Apr. 12, 2012

(65) Prior Publication Data
US 2013/0303638 A1    Nov. 14, 2013

(30) Foreign Application Priority Data
Oct. 5, 2010  (DE) .......................... 10 2010 037 980

(51) Int. Cl.
*C07C 1/06* (2006.01)
*C10L 3/08* (2006.01)
*B01J 8/04* (2006.01)

(52) U.S. Cl.
CPC ................. *C10L 3/08* (2013.01); *B01J 8/0453* (2013.01); *B01J 8/0492* (2013.01); *C07C 1/06* (2013.01)

(58) Field of Classification Search
CPC ............... C07C 1/06; C07C 9/04; C10L 3/08; B01J 8/0453; B01J 8/0492
USPC .......................................... 518/706; 422/607
See application file for complete search history.

(56) References Cited

U.S. PATENT DOCUMENTS 3,967,936 A * 7/1976 Tajbl et al. .................. 48/197 R
8,225,898 B2   7/2012 Kuwabara
2010/0078256 A1 4/2010 Kuwabara

FOREIGN PATENT DOCUMENTS

GB     2018818 A    10/1979

* cited by examiner

*Primary Examiner* — Jafar Parsa
*Assistant Examiner* — Amy C Bonaparte
(74) *Attorney, Agent, or Firm* — Andrew Wilford

(57) ABSTRACT

A methane-rich gas from synthesis gas is made in a methane reactor with a row of methanation stages and, at an upstream end of the row of methanation stages, a CO conversion stage. An incoming stream of synthesis gas containing CO and $H_2$ is split into a plurality of partial streams, one of which is fed to the reactor upstream of the CO conversion stage. Each of the other partial syngas streams is fed to the reactor upstream of a respective one of the methanation stages such that methanation takes place in each of the methanation stages and gas exits from the stages and mixes with the partial syngas stream being fed to the next downstream stage. A plurality of partial streams are diverted from a product-gas stream issuing from the furthest downstream stage and are each fed to the reactor upstream of a respective one of the methanation stages.

12 Claims, 1 Drawing Sheet

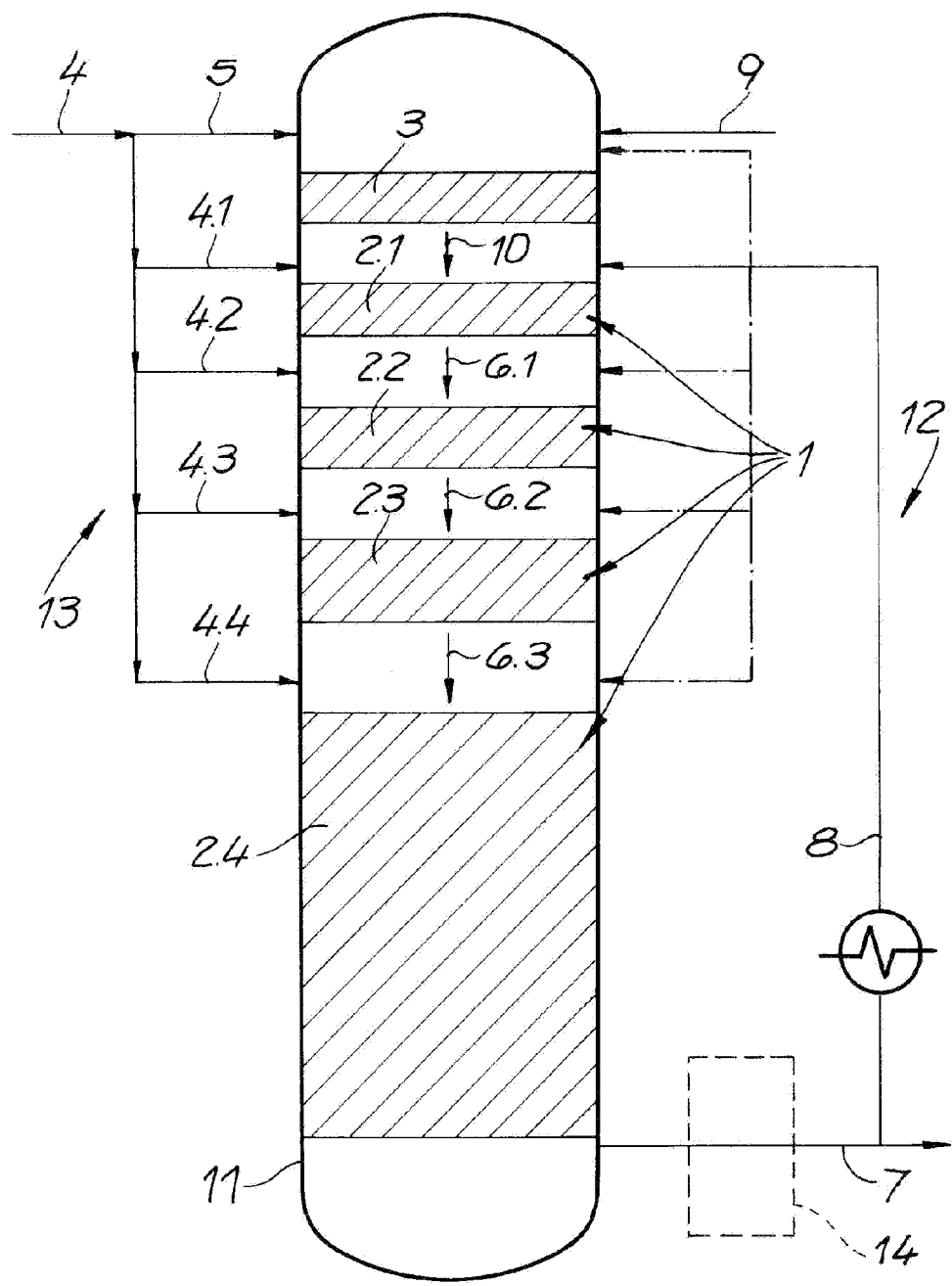

METHOD AND APPARATUS FOR MAKING A METHANE-RICH GAS FROM SYNGAS

CROSS REFERENCE TO RELATED APPLICATIONS

This application is the US-national stage of PCT application PCT/EP2011/067369 filed 5 Oct. 2011 and claiming the priority of German patent application 102010037980.8 itself filed 5 Oct. 2010.

FIELD OF THE INVENTION

The invention relates to a method for making a methane-rich gas from synthesis gas, wherein a synthesis gas containing CO and $H_2$ is mixed with a gas stream that is diverted from methane-rich product gas and returned thereto, and is then passed through a catalyst bed consisting of a methanation catalyst, wherein methanation takes place in the catalyst bed and the gas stream is heated by released reaction heat. The invention further relates to a methanation reactor for carrying out the method.

BACKGROUND OF THE INVENTION

Catalysts containing nickel are used as the methanation catalysts, in which the active substance containing the nickel is bonded to carrier materials, for example of aluminum oxide, silicon oxide, zirconium oxide and similar. The primary, exothermic methanation reactions that take place the catalyst bed are as follows:

$$CO + 3H_2 \leftrightarrows CH_4 + H_2O$$

$$CO_2 + 4H_2 \leftrightarrows CH_4 + 2H_2O$$

The formation of methane is accompanied by the generation of considerable heat, so that the temperatures of the reagents and the products rise as they pass through the catalyst bed. At the same time, as the temperatures rise, the equilibrium concentration of methane falls. The higher the temperature of the gas stream leaving the catalyst bed, the lower the methane content in the gas stream, correspondingly with the reaction equilibrium underlying the reaction equations given above. For this reason, in methanation reactions the reaction temperature should be kept as low as possible. The definition of a suitable temperature for the synthesis gas as it enters the catalyst bed is determined by other criteria, however. It must be borne in mind that as the temperature is lowered, the reaction rate becomes slower. In particular, it must also be noted that an inlet temperature lower than 290° C. can lead to irreversible damage to the nickel catalyst, caused as far as is known according to current understanding by a reaction between nickel and carbon monoxide to form nickel carbonyl.

In a method known from DE 29 14 806 [GB 2,018,818], which serves as the starting point for this invention, a CO conversion stage is connected upstream from the catalyst bed, which consists of a methanation catalyst, the purpose of the conversion stage being to reduce the CO content in the feed gas and thus lower the CO partial pressure to such a point that the carbonyl so damaging to the catalyst cannot form. In the conversion stage, a catalytic shift reaction takes place according to the following reaction equation $$CO + H_2O \leftrightarrows CO_2 + H_2$$

The catalyst for the CO conversion stage, which is also called a shift catalyst, contains for example two of the metals Cu, Zn and Cr, which themselves are bonded on a carrier. In the known method, both the entire synthesis gas stream and the recirculated gas stream that is split off from the product gas for cooling purposes are passed through the CO conversion stage. The shift catalyst takes up as much as 75% of the entire volume of the catalyst that is required for the methanation reactions and CO conversion, and accordingly requires significant effort in terms of technical equipment. Since the shift reaction is also exothermic, the synthesis gas is heated up during the CO conversion, so the temperature of the synthesis gas stream at the inlet to the methanation reactor rises, which also raises the outlet temperature, with the result that a low temperature at the inlet temperature into the catalytic CO shift bed is can only be used to a certain degree.

OBJECT OF THE INVENTION

The object of the invention is to improve the effectiveness of the methanation method.

SUMMARY OF THE INVENTION

This object is solved according to the invention in that the catalyst bed is divided into several methanation stages, and the gas flows through them one after the other. The synthesis gas is split correspondingly into partial streams, each of which is fed to the catalyst bed of an assigned methanation stage, wherein the gas that exits a methanation stage, and that has been heated up by the methanation reactions in the stage is mixed with the colder partial stream of synthesis gas for the following methanation stage, and is cooled thereby, and wherein the resulting mixed gas stream is fed to the catalyst bed in the subsequent methanation stage as feed gas. An arrangement whereby the synthesis gas streams are directed variously to the individual catalyst stages also particularly falls within the scope of the invention. In this context, it is particularly advantageous to increase the quantity of synthesis gas successively from one catalyst stage to the next, since the product gas stream from the preceding methanation stage in each case also has a moderating function on the reaction temperature similar to the effect with the returned final gas product stream.

With this method arrangement with incremented quantities it is possible to cool each volume of methane-rich product gas exiting from a methanation stage effectively with the partial stream of synthesis gas provided for the next methanation stage. Therefore, the partial streams of synthesis gas are preferably fed in at a temperature of less than 250° C., for example at a temperature between about 100° C. and 200° C., and mixed with the methane-rich gas exiting from the preceding methanation stage. By this direct cooling, most of the reaction heat generated in the methanation reaction may be removed from the gas, which in turn means that the quantity of gas diverted from and returned to the product gas may be reduced. Temperature control in the methanation stages may also be improved and the temperature at the outlet from the methanation stages may be reduced, thus resulting in better equilibrium conversion in the methanation reactions. The inventive method of separating the synthesis gas stream so that partial gas streams flow through multiple methanation stages one after the other and the use of direct gas cooling enable the methanation reactions to be conducted at a lower temperature level. Consequently, the quantity of converted methane increases as more methanation stages are added.

The gas stream that is split off from the methane-rich product gas and then returned to it may be fed to the catalyst bed in the first methanation stage. An advantageous embodiment of the method according to the invention, which helps to improve the method further, provides that the gas stream that is split off from the product gas and then returned to it is itself divided into partial streams, which may then be fed to the respective methanation stages. After the second methanation stage, the temperature of the feed gas introduced should be adjusted such that the temperature of the mixed gas reaches at least 300° C. It is advisable for the returned gas stream to be cooled. The temperatures and volume flows of the gas streams that are merged before a methanation stage must also be balanced with each other in such a way, taking into account the methanation reactions that take place in the next methanation stage, that methane-rich gas exiting the methanation stage has an outlet temperature of 600° C. to 850° C. preferably lower than 800° C.

The quantity of the gas stream fed to the first methanation stage is preferably 2 to 4 times greater than the quantity of synthesis gas that is fed to the first methanation stage as a partial stream of the total synthesis gas stream. Less than 10%, preferably from 2% to 5% of the synthesis gas may be fed to the first methanation stage as feed gas.

A particularly preferred embodiment of the method according to the invention provides that a CO conversion stage with a CO conversion catalyst is installed upstream of the first methanation stage, and that a partial synthesis gas stream is split off from the synthesis gas, this partial stream being fed to the CO conversion stage. In the conversion stage, a shift catalyst that does not contain any parts that can form metal carbonyls is used. Usual and suitable shift catalysts contain combinations of the metals copper, zinc and chromium. According to the invention, it is not the entire stream of synthesis gas that is fed through the CO conversion stage, but advantageously only a partial stream that has been split off from the synthesis gas, constituting less than 10% of the total quantity of synthesis gas. Preferably, only 2% to 5% of the synthesis gas, having an inlet temperature from 200° C. to 250° C., is introduced into the catalyst bed in the CO conversion stage, which bed is constituted of a shift catalyst. If necessary, the CO present in the feed gas is converted to $CO_2$ and steam by the addition of live steam. In this way, the concentration of the CO present in the small quantity of feed gas is lowered significantly, thus making it practically impossible for nickel carbonyl to form in the subsequent methanation stage.

Besides method steam, a methane-rich recirculated gas with preferably more than 60% by volume may also be fed to the CO conversion stage as the product gas. In this context, the product gas may also originate from methanation reactors located downstream of the methanation stages described here. The methane-rich recirculated gas stream, or a partial stream thereof may also be mixed with the gas stream exiting the CO conversion stage, in which case according to a preferred embodiment the total quantity of the gas stream fed into the first CO conversion stage and the first methanation stage is equivalent to between 2 and 4 times as much as the quantity of synthesis gas that is fed to the CO conversion stage and the first methanation stage as a partial stream of the total synthesis gas stream. In the following, this ratio will also be referred to as the recirculation ratio. As a result of the recirculation ratio of this magnitude of preferably 2 to 4 according to the invention, the CO content in the mixed gas is lowered further by dilution. A corresponding adjustment of the recirculation ratio enables a mixing temperature to be set for the mixed gas from the product gas of the CO conversion, the synthesis gas stream that is fed in, and the returned product gas stream that is higher than or equal to the light-off temperature for the subsequent methanation, and is for example between 250° C. and 400° C. depending on the catalyst type used.

BRIEF DESCRIPTION OF THE DRAWING

In the following, the invention will be explained in greater detail with reference to just one FIGURE representing an exemplary embodiment thereof. The single FIGURE is a schematic representation of a methanation reactor for making a methane-rich gas from synthesis gas.

SPECIFIC DESCRIPTION OF THE INVENTION

The methanation reactor includes a catalyst bed 1 made from a nickel-containing methanation catalyst, wherein catalyst bed 1 is divided into multiple methanation stages 2.1 to 2.4, through which gas passes one after the other. A CO conversion stage 3 with a CO conversion catalyst, also called a shift catalyst, is connected upstream from first methanation stage 2.1. The FIGURE shows that a synthesis gas 4 containing Co and $H_2$ is divided into partial syngas streams 4.1 to 4.4, 5, wherein partial stream 5 is fed to the CO conversion stage and the other partial streams 4.1 to 4.4 are each fed to the catalyst bed of an assigned methanation stage 2.1 to 2.4. The gas 6.1 to 6.3 that exits a methanation stage, and which has been heated by methanation reactions, is mixed with the synthesis gas partial stream 4.2 to 4.4 for the subsequent methanation stage, and is cooled thereby. The resulting stream of mixed gas is fed to the catalyst bed of the subsequent methanation stage as feed gas.

A gas stream 8 is split off from the methane-rich product gas 7 and returned to the methanation reactor. In the embodiment, returned gas stream 8 is fed to the catalyst bed of first methanation stage 2.1. Optionally, it is also possible for the gas stream split off from product gas 7 and returned to be split into partial product-gas streams each fed to a respective one of the methanation stages 2.1 to 2.4. The returned gas stream 8 is cooled.

The volume flows and temperatures of the gas streams are balanced with each other in such manner that the mixed gas streams at the inlets to the second and each subsequent methanation stage 2.2 to 2.4 have a mixed gas temperature of at least 300° C. Moreover, the temperatures and volumes flows of the gas streams that are merged before a methanation stage are balanced with each other in such a way, taking into account the methanation reactions that take place in the next methanation stage, that methane-rich gas 6.1 to 6.3 exiting the methanation stage has an outlet temperature of 600° C. to 850° C. preferably about 800° C.

The quantity of synthesis gas partial stream 5 that is fed to the CO conversion stage is preferably in the range between 2% and 5% of total volume of synthesis gas that is introduced as feed gas. When water vapor (live steam) 9 is added, the CO in the feed gas is converted to $CO_2$ and hydrogen. The CO content in gas stream 10 is reduced by CO conversion to such an extent that in the subsequent methanation stage 2.1 there is not enough to form the nickel carbonyl that damages the catalyst.

Gas stream 10 that exits CO conversion stage 3 is mixed with a recirculating gas stream 8 that has been split off from the methane-rich product gas, wherein the quantity of the recirculating gas stream 8 is two to four times greater than the quantity of the gas stream that is created by mixing the gas stream 10 exiting the CO conversion stage and the synthesis gas partial stream 4.1 being fed to first methanation stage 2.1. In the following, this ratio will also be referred to as the recirculation ratio. By appropriate selection of the recirculation ratio, the CO content in the mixed gas, which is fed to first methanation stage 2.1, may be reduced to such a level that formation of the nickel carbonyl that would damage the catalyst is impossible.

The mixed gas is now fed to the catalyst bed of first methanation stage 2.1, which is arranged underneath CO conversion catalyst 3. When methanation takes place here, it is associated with heating of the gas stream to temperatures between 600° C. and 800° C. A further synthesis gas partial stream 4.2 is added to the methane-rich product gas that exits the catalyst bed of methanation stage 2.1, and a mixing temperature higher than 300° C. is set. This ensures that the methanation catalyst cannot be damaged by the formation of nickel carbonyl. In order to adjust the temperature of the mixed gas further, or also to lower the outlet temperature from the following methanation stage 2.2, a partial stream split off from recirculating gas 8 may be fed to mixed gas before the mixed gas is fed into second methanation stage 2.2. Second methanation stage 2.2 also has a catalyst bed consisting of a methanation catalyst. Here, methanation takes place and the temperature in the gas stream rises.

The method described is repeated in one or more additional methanation stages.

The methanation reactor in the FIGURE for carrying out the method described includes a housing 11, a plurality of methanation stages 2.1 to 2.4 arranged inside the housing, each of which has a catalyst bed consisting of a methanation catalyst, a plurality of synthesis gas inlets for feeding in synthesis gas 4, a product gas outlet and a device 12 for recirculating gas of a product gas partial stream to the inlet side of first methanation stage 2.1. At least one synthesis gas inlet is arranged upstream of each methanation stage 2.1 to 2.4. The synthesis gas inlets are interconnected via a flow distributor 13, which splits synthesis gas 4 into synthesis gas partial streams 4.1 to 4.4 and feeds them to methanation stages 2.1 to 2.4.

The FIGURE shows that housing 11 is constructed in the form of an erect apparatus, through which the gas flows from top to bottom, and chambers without catalysts, to which the synthesis gas inlets are connected, are provided between methanation stages 2.1 to 2.4. The chambers without catalysts may contain mixing elements, such as bead beds, packing beds and similar consisting of inert materials which ensure that the respective product gases from the individual catalyst beds are mixed well with the gases that are added.

Splitter lines may be connected to device 12 for recirculating the gas, wherein at least one splitter line upstream of each of methanation stages 2.1 to 2.4 leads to housing 11.

A CO conversion stage 3 having a catalyst layer consisting of a CO conversion catalyst is connected upstream of, and in this FIGURE above, methanation stage 2.1. A synthesis gas inlet through which a synthesis gas partial stream 5 may be fed is arranged upstream of the catalyst bed of conversion stage 3. Additionally, a steam line for introducing live steam opens into the area before the catalyst bed of the CO conversion catalyst. In the exemplary embodiment, a splitter line that opens into the housing upstream of conversion stage 3 is also connected to device 12 and enables the conversion stage as well to be charged with a fraction of the recirculating gas. The gases fed in (5, 4.1 to 4.4, 12) are mixed with the gas streams (10, 6.1 to 6.3) exiting from the respective catalyst beds by means of mixing elements such as a bed of inert beads or other mixing elements. Since the volume of the gas stream increases from the top down, the height of the catalyst bed required for the synthesis gas conversion becomes progressively greater, though the replaced beds need relatively little catalyst because of the gas quantity, which is initially quite small. This also is particularly true for the CO catalyst bed.

Recirculating gas 8 is transported away after methanation stages 2.1 to 2.4, in the direction of flow, that is to say downstream from housing 11. In this regard, it is indicated in the single FIGURE that recirculating gas 8 may also be passed through further, only schematically suggested methanation reactors 14 before it is discharged. Of course, the line systems with the feed lines, splitter lines and similar are also represented schematically, and in particular may be equipped with means for flow control to assist with setting the desired flow conditions.

The invention claimed is:

1. A method of making a methane-rich gas from synthesis gas, the method comprising the steps of:
dividing a catalyst bed in a reactor into a plurality of methanation stages arranged one downstream of the other;
providing in the reactor upstream of the furthest upstream methanation stage a CO conversion stage with a CO conversion catalyst;
splitting an incoming stream of synthesis gas containing CO and H$_2$ into a plurality of partial syngas streams, one of the partial syngas streams containing less than 10% of the incoming stream;
feeding the one partial syngas stream to the reactor upstream of the CO conversion stage;
feeding each of the other partial syngas streams to the reactor upstream of a respective one of the methanation stages such that gas exits each stage and passes through the next downstream methanation stage and the gas exiting the furthest downstream methanation stage forms a product-gas stream;
splitting from the product gas stream a plurality of partial product-gas streams;
feeding each of the partial product-gas streams to the reactor upstream of a respective one of the methanation stages such that the gas that exits the methanation stages and that has been heated up by methanation reactions therein mixes with and is cooled by the respective partial syngas stream fed to the following methanation stage and the resulting mixed gas stream passes through the subsequent methanation stage as a feed gas.

2. The method as recited in claim 1, further comprising the step of:
setting a mixed gas temperature of at least 300° C. in the feed gas that is fed to a methanation stage.

3. The method as recited in claim 1, wherein another one of the partial product-gas streams is fed to the furthest upstream methanation stage in a quantity equal to 2 to 4 times the quantity of synthesis gas that is fed in the one partial syngas stream to the CO conversion stage.

4. The method as recited in claim 1, wherein from 2% to 5% of the incoming synthesis gas stream is fed as another partial syngas stream to the furthest upstream methanation stage as feed gas.

5. The method as recited in claim 1, further comprising the step of:
balancing the temperatures and volume flows of the gas streams that are merged before a methanation stage with each other in such a way, taking into account the methanation reactions that take place in the next methanation stage, that the methane-rich gas exiting the methanation stage has an outlet temperature of 600° C. to 850° C.

6. The method as recited in claim 1, further comprising the step of:
feeding live steam to the reactor upstream of the CO conversion stage.

7. The method as recited in claim 1, wherein the one partial syngas stream is fed to the CO conversion stage at a temperature from 200° C. to 250° C.

8. The method as recited in claim 7, further comprising the step of:
   feeding a partial product-gas stream to the reactor upstream of the CO conversion stage.

9. The method as recited in claim 7, further comprising the step of:
   making the total quantity of the gas in the partial product-gas stream returned to the CO conversion stage and the furthest upstream methanation stage equivalent to between 2 and 4 times as much as the quantity of synthesis gas that is fed to the CO conversion stage and to the furthest upstream methanation stage as a partial syngas stream.

10. The method as recited in claim 1, further comprising the step of setting the volume or rate at which each partial syngas stream and the volume or rate at which each partial product-gas stream are introduced into the reactor such that a mixture of product gas, synthesis gas, and gases issuing from a methanation stage has, before it enters the following methanation stage, a mixture temperature higher than or equal to an ignition temperature for the methanation in the following methanation stage and is higher than 300° C.

11. The method as recited in claim 1, further comprising the step of:
   introducing the partial syngas streams at a temperature of less than 250° C. to cool the partial product-gas streams with which they mix in the reactor.

12. A method of making a methane-rich gas from synthesis gas, the method comprising the steps of:
   providing a methane reactor with a row of methanation stages and, at an upstream end of the row of methanation stages, with a CO conversion stage;
   splitting from an incoming stream of synthesis gas containing CO and $H_2$ a plurality of partial syngas streams, one of the partial syngas streams holding less than 10% of the incoming stream;
   feeding the one partial syngas stream to the reactor upstream of the CO conversion stage;
   feeding each of the other partial syngas streams to the reactor upstream of a respective one of the methanation stages such that methanation takes place in each of the methanation stages and gas exits from the CO conversion stage and from each of the methanation stages and mixes with the partial syngas stream being fed to the next downstream stage and a product-gas stream issues from the furthest downstream stage; and
   diverting from the product-gas stream a plurality of partial product-gas streams and feeding each of the product gas streams to the reactor upstream of a respective one of the methanation stages.

* * * * *